US008454529B2

(12) United States Patent
Daly et al.

(10) Patent No.: US 8,454,529 B2
(45) Date of Patent: Jun. 4, 2013

(54) MINIMIZATION OF ELECTRICAL STIMULUS ARTIFACT DURING MEASUREMENT OF EVOKED NEURAL RESPONSE

(75) Inventors: Christopher N. Daly, Bilgola Plateau (AU); Tony M. Nygard, Terrigal (AU); Helmut C. Eder, Castle Hill (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 11/802,756

(22) Filed: May 24, 2007

(65) Prior Publication Data

US 2007/0225767 A1 Sep. 27, 2007

Related U.S. Application Data

(63) Continuation of application No. 10/475,141, filed as application No. PCT/AU02/00500 on Apr. 18, 2002, now abandoned.

(30) Foreign Application Priority Data

Apr. 18, 2001 (AU) .................................... PR4462
Aug. 17, 2001 (AU) .................................... PR7111

(51) Int. Cl.
*A61B 5/04* (2006.01)
*A61B 5/05* (2006.01)
*A61B 5/053* (2006.01)
*A61B 5/00* (2006.01)
*A61N 1/05* (2006.01)

(52) U.S. Cl.
USPC ........... 600/554; 600/544; 600/545; 600/559; 607/30; 607/57; 607/62

(58) Field of Classification Search
USPC .................. 600/544, 545, 554, 559; 607/30, 607/57, 62
See application file for complete search history.

(56) References Cited

U.S. PATENT DOCUMENTS

| 4,114,627 | A | | 9/1978 | Lewyn et al. |
|---|---|---|---|---|
| 4,305,396 | A | | 12/1981 | Wittkampf et al. |
| 4,343,312 | A | | 8/1982 | Cals et al. |
| 4,373,531 | A | | 2/1983 | Wittkampf et al. |
| 4,510,936 | A | * | 4/1985 | Fourcin et al. ................. 607/57 |
| 4,532,930 | A | | 8/1985 | Crosby et al. |
| 4,543,956 | A | * | 10/1985 | Herscovici ..................... 607/13 |
| 4,821,724 | A | * | 4/1989 | Whigham et al. .............. 607/13 |

(Continued)

FOREIGN PATENT DOCUMENTS

| EP | 0 282 336 A2 | 11/1988 |
|---|---|---|
| WO | WO 92/10134 | 6/1992 |

(Continued)

OTHER PUBLICATIONS

AU Examiner's Report No. 2 for AU 2002248990 dated Apr. 12, 2007, 2 pages total.

(Continued)

*Primary Examiner* — Sean Dougherty
(74) *Attorney, Agent, or Firm* — Kilpatrick, Townsend & Stockton, LLP.

(57) ABSTRACT

The invention provides a method of electrical artefact compensation in measurement of a neural response. The neural response is evoked by a first stimulus, after which a compensatory stimulus is applied in order to counteract a stimulus artefact caused by the first stimulus. The invention also provides for short circuiting the stimulating electrode subsequent to the first stimulus. A system for implementing such steps is also provided. The invention may be of application in measurement of physiological responses, including neural responses and in particular a neural response of the auditory nerve.

29 Claims, 9 Drawing Sheets

U.S. PATENT DOCUMENTS

| | | | |
|---|---|---|---|
| 4,895,152 A * | 1/1990 | Callaghan et al. | 607/13 |
| 4,969,460 A * | 11/1990 | Callaghan et al. | 607/28 |
| 5,016,280 A | 5/1991 | Engebretson | |
| 5,034,918 A | 7/1991 | Jeong | |
| 5,139,028 A * | 8/1992 | Steinhaus et al. | 600/510 |
| 5,172,690 A | 12/1992 | Nappholz et al. | |
| 5,184,615 A * | 2/1993 | Nappholz et al. | 607/14 |
| 5,278,994 A | 1/1994 | Black et al. | |
| 5,565,503 A | 10/1996 | Leysieffer et al. | |
| 5,674,264 A * | 10/1997 | Carter et al. | 607/57 |
| 5,741,312 A * | 4/1998 | Vonk et al. | 607/28 |
| 5,758,651 A | 6/1998 | Nygard et al. | |
| 5,810,725 A * | 9/1998 | Sugihara et al. | 600/372 |
| 5,861,013 A * | 1/1999 | Peck et al. | 607/28 |
| 5,873,898 A * | 2/1999 | Hemming et al. | 607/28 |
| 5,895,416 A | 4/1999 | Barreras et al. | |
| 5,963,904 A | 10/1999 | Lee et al. | |
| 6,035,001 A | 3/2000 | Eklund et al. | |
| 6,044,162 A | 3/2000 | Mead et al. | |
| 6,151,400 A | 11/2000 | Seligman | |
| 6,157,861 A | 12/2000 | Faltys et al. | |
| 6,201,993 B1 * | 3/2001 | Kruse et al. | 607/30 |
| 6,205,360 B1 * | 3/2001 | Carter et al. | 607/57 |
| 6,231,521 B1 * | 5/2001 | Zoth et al. | 600/559 |
| 6,249,704 B1 * | 6/2001 | Maltan et al. | 607/57 |
| 6,427,085 B1 * | 7/2002 | Boon et al. | 607/28 |
| 6,428,484 B1 | 8/2002 | Battmer et al. | |
| 6,430,402 B1 | 8/2002 | Agahi-Kesheh | |
| 6,463,328 B1 | 10/2002 | John | |
| 6,537,200 B2 | 3/2003 | Leysieffer et al. | |
| 6,565,503 B2 | 5/2003 | Leysieffer et al. | |
| 6,575,894 B2 | 6/2003 | Leysieffer et al. | |
| 6,587,724 B2 * | 7/2003 | Mann | 607/30 |
| 6,600,955 B1 * | 7/2003 | Zierhofer | 607/57 |
| 6,697,674 B2 | 2/2004 | Leysieffer | |
| 6,751,505 B1 * | 6/2004 | Van Den Honert et al. | 607/57 |
| 6,892,092 B2 * | 5/2005 | Palreddy et al. | 600/509 |
| 7,089,049 B2 * | 8/2006 | Kerver et al. | 600/515 |
| 7,171,261 B1 * | 1/2007 | Litvak et al. | 600/544 |
| 7,174,213 B2 * | 2/2007 | Pless | 607/45 |
| 7,206,640 B1 * | 4/2007 | Overstreet | 607/57 |
| 7,251,530 B1 * | 7/2007 | Overstreet et al. | 607/55 |
| 7,277,759 B2 * | 10/2007 | Overstreet et al. | 607/56 |
| 7,317,945 B2 * | 1/2008 | Litvak et al. | 607/57 |
| 7,317,948 B1 * | 1/2008 | King et al. | 607/62 |
| 7,403,820 B2 * | 7/2008 | DiLorenzo | 607/45 |
| 7,577,480 B2 * | 8/2009 | Zeijlemaker | 607/11 |
| 7,953,481 B1 * | 5/2011 | Shemer et al. | 607/14 |
| 2001/0049466 A1 | 12/2001 | Baumann et al. | |
| 2004/0098063 A1 | 5/2004 | Goetz | |
| 2005/0101878 A1 | 5/2005 | Daly et al. | |
| 2005/0245991 A1 | 11/2005 | Faltys et al. | |

FOREIGN PATENT DOCUMENTS

| | | |
|---|---|---|
| WO | WO 93/24176 | 12/1993 |
| WO | WO 94/14376 | 7/1994 |
| WO | WO 95/01709 | 1/1995 |
| WO | WO 96/12383 | 4/1996 |
| WO | WO 97/09863 | 3/1997 |
| WO | WO 97/48447 | 12/1997 |
| WO | WO 00/76436 | 12/2000 |
| WO | 01/06810 | 1/2001 |
| WO | WO 01/13991 | 3/2001 |
| WO | WO 02/082982 | 10/2002 |
| WO | WO 03/070322 | 8/2003 |
| WO | WO 2004/021885 | 3/2004 |

OTHER PUBLICATIONS

AU Examiner's First Report No. for AU 2007201637 dated Jan. 17, 2008, 2 pages total.

EP Examiner's Report for EP 02 717 863 dated Jan. 20, 2009, 5 pages total.

Brown, et al., The Relationship Between EAP and EABR Thresholds and Levels Used to Program the Nucleus 24 Speech Processor: Data from Adults, *Ear and Hearing*, vol. 21 (2), Apr. 2000, pp. 151-163.

Charasse, et al., "Automatic analysis of auditory nerve electrically evoked compound action potential with an artificial neural network," *Artificial Intelligence in Medicine*, 2004 31, 221-229.

Delgado, et al, "Automated Auditory Brainstem Response Interpretation," *IEEE Engineering in Medicine and Biology*, Apr./May 1994.

Charasse, et al., "Comparison of Two Different Methods to Automatically Classify Auditory Nerve Responses Recorded with NRT System," *Acta Acustica United with Acustica*, vol. 99 (2004) 512-519.

Seyle, et al., "Speech Perception Using Maps Based on Neural Response Telemetry Measures," *Ear & Hearing*, Copyright © 2002 by Lippincott Williams & Wilkins.

Vannier, et al., "Objective detection of brainstem auditory evoked potentials with a priori information from higher presentation levels," *Artificial Intelligence in Medicine* 25, (2002) 283-301.

Franck, et al., Estimation of Psychophysical Levels Using the Electrically Evoked Compound Action Potential Measured with the Neural Response Telemetry Capabilities of Cochlear Corporation's C124M Device, *Ear & Hearing*, Copyright © 2001 by Linniocott Williams & Wilkins.

Hughes, et al, Comparison of EAP Thresholds with MAP Levels in the Nucleus 24 Cochlear Implant: Data from Children [Articles], *Ear and Hearing*, vol. 21 (2), Apr. 2000, pp. 164-174.

Cohen, et al., "Spatial spread of neural excitation in cochlear implant recipients: comparison of improved ECAP method and psychophysical forward masking," *Hearing Research*, 179 (2003) 72-87.

Cohen, et al., "Spatial spread of neural excitation: comparison of compound action potential and forward-masking data in cochlear implant recipients," *International Journal of Audiology 2004*: 43: 346-355.

Miller, et al., "An Improved Method of Reducing Stimulus Artifact in the Electrically Evoked Whole-Nerve Potential," *Ear & Hearing*, Copyright © 2000 by Lippincott Williams & Wilkins, USA.

European Search Report, EP 01 95 9971, dated Aug. 11, 2005.

International Preliminary Examination Report, PCT/AU01/01032, dated Apr. 10, 2002.

International Search Report, PCT/AU01/01032, dated Oct. 5, 2001.

International Search Report and Written Opinion, PCT/US05/21207 dated Feb. 8, 2006.

International Preliminary Examination Report, PCT/AU02/00500, dated Feb. 12, 2003.

International Search Report, PCT/AU02/00500, dated Jun. 26, 2002.

Supplementary Partial European Search Report, EP 02 71 7863 dated Oct. 18, 2005.

Hartmann, et al., "Evoked Potentials from the Auditory Nerve Following Sinusoidal Electrical Stimulation of the Cochlea: New Possibilities for Preoperative Testing in Cochlear-Implant Candidates?" *Acta Otoloaryngol (Stockh)* 1994; 114, Scandinavian University Press ISSN 0001-648, pp. 495-500.

Bas van Dijk, "Development of a prototype fully-automated intraoperative ECAP recording tool, using NRT(TM) v3", 2003 Conference on Implantable Auditory Prosthesis. 2003.

Paul J. Abbas, "Electrically Evoked Compound Action Potentiais Recorded from Subjects Who Use the Nucieus C12M Device", Ann Otol Rhinol Laryngol Suppl. 185:6-9; Dec. 2000.

Frank Baumgarte et al., "A Nonlinear Psychoacoustic Model Applied to the ISO MPEG Layer 3 Coder", 99th AES Convention, New York, Oct. 1995.

Bernd Edler et al., "ASAC—Analysis/Synthesis Audio Codec for Very Low Bit Rates", 100th AES Convention, Copenhagen; May 1996.

* cited by examiner

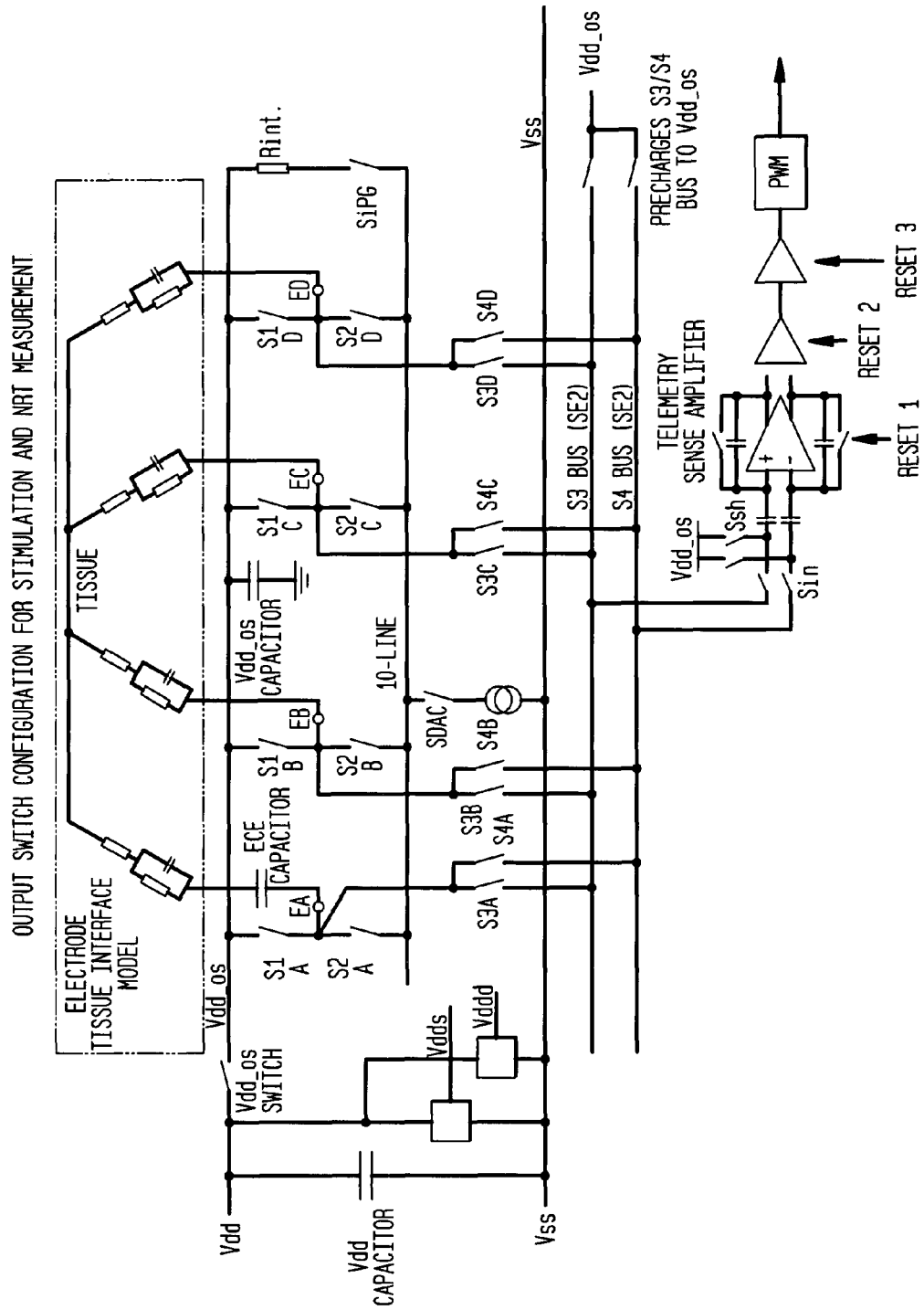
FIG. 3 OUTPUT SWITCH CONFIGURATION FOR STIMULATION AND NRT MEASUREMENT FIG. 6A
OBTAINING THE MEASUREMENT FOR DECISION
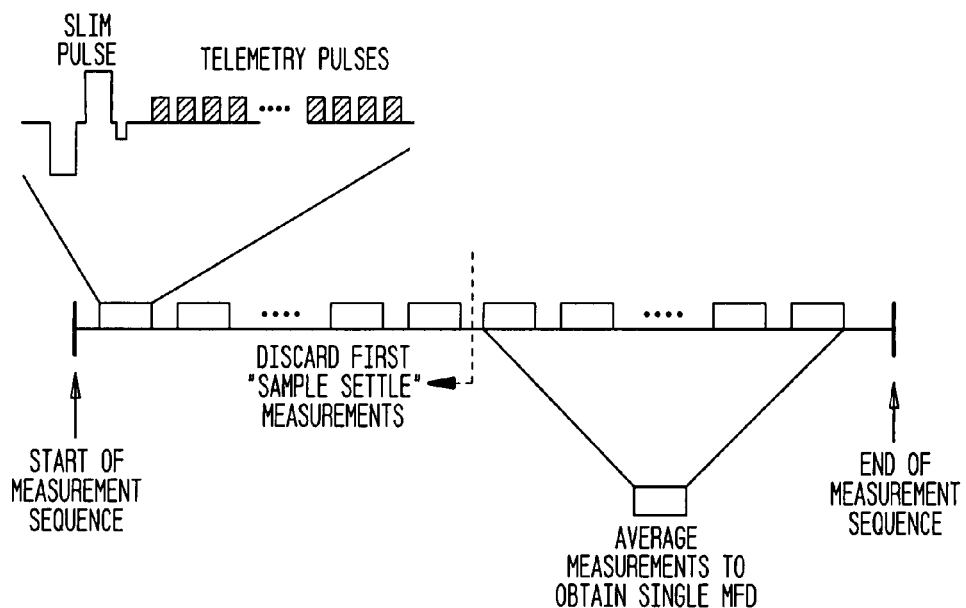
FIG. 6B
RESULTS OF INITIAL MFD TAKEN WITH 3RD PHASE=0
NRT AMPLIFIER MEASUREMENT WINDOW
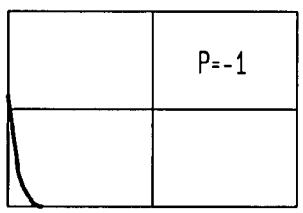
NEGATIVE ERROR MEANS INCREASING
3RD PHASE MOVES MEASUREMENT "UP"
NRT AMPLIFIER MEASUREMENT WINDOW
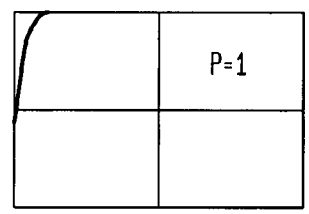
POSITIVE ERROR MEANS INCREASING 3RD
PHASE MOVES MEASUREMENT "DOWN"

MINIMIZATION OF ELECTRICAL STIMULUS ARTIFACT DURING MEASUREMENT OF EVOKED NEURAL RESPONSE

CROSS-REFERENCE TO RELATED APPLICATIONS

This application is a continuation of U.S. patent application Ser. No. 10/475,141 filed on Oct. 17, 2003, entitled, "Minimization of Electrical Stimulus Artifact During Measurements of Evoked Neural Response," which is a national stage application of PCT/AU2002/00500 filed Apr. 18, 2002, which claims priority from Australian Application No. PR 4462 filed Apr. 18, 2001, and Australian Application No. PR 7111 filed Aug. 17, 2001.

FIELD OF THE INVENTION

The present invention relates to a method and apparatus for measuring the evoked responses of nerves to electrical stimulation, and more particularly to a system and apparatus to assist recovery of such data from an auditory prosthesis.

DESCRIPTION OF THE PRIOR ART

Cochlear implants have been developed to assist people who are profoundly deaf or severely hearing impaired, by enabling them to experience hearing sensation representative of the natural hearing sensation. In most such cases, these individuals have an absence of or destruction of the hair cells in the cochlea which naturally transduce acoustic signals into nerve impulses which are interpreted by the brain as sound. The cochlear implant therefore bypasses the hair cells to directly deliver electrical stimulation to the auditory nerves with this electrical stimulation being representative of the sound.

Cochlear implants have traditionally consisted of two parts, an external speech processor unit and an implanted stimulator/receiver unit. The external speech processor unit has been worn on the body of the user and its main purpose has been to detect the external sound via a microphone and convert the detected sound into a coded signal through an appropriate speech processing strategy.

This coded signal is then sent to the receiver/stimulator unit which is implanted in the mastoid bone of the user, via a transcutaneous link. The receiver/stimulator unit then processes this coded signal into a series of stimulation sequences which are then applied directly to the auditory nerve via a series of electrodes positioned within the cochlea, proximal to the modiolus of the cochlea.

As the implant is surgically implanted within the recipient, there is a need to obtain data about the actual performance of the electrode array following implantation as well as the response of the auditory nerve to stimulation. Such data collection enables detection and confirmation of the normal operation of the device, and allows the stimulation parameters to be optimised to suit the needs of the patient.

Typically, following the surgical implantation of the cochlear implant, the recipient must have the implant fitted or customised to conform with the specific recipient demands. This procedure collects and determines patient specific parameters such as threshold levels (T levels) and maximum comfort levels (C levels) for each stimulation channel. Essentially, this is manually performed by applying stimulation pulses for each channel and receiving an indication from the implant recipient as to the level and comfort of the resulting sound. For implants with a large number of channels for stimulation, this process is quite time consuming and rather subjective as it relies heavily on the recipient's subjective impression of the stimulation rather than any specific measurement. This aspect is further complicated in the case of children and prelingually or congenitally deaf patients who are unable to supply an accurate impression of the resultant hearing sensation, and hence fitting of the implant may be sub-optimal. In such cases an incorrectly fitted implant may result in the recipient not receiving optimum benefit from the implant and in the cases of children may directly hamper the speech and hearing development of the child.

Therefore, as previously mentioned, there is a need to obtain objective measurements of patient specific data especially in cases where an accurate subjective measurement is not possible.

One proposed method of interrogating the performance of the implanted device and making objective measurements of patient specific data such as T and C levels is to directly measure the response of the auditory nerve to an electrical stimulus. The measurement of Electrically Evoked Compound Action Potentials (ECAPs) provides an objective measurement of the response of the nerves to electrical stimulus. Following electrical stimulation, the neural response is caused by the superposition of single neural responses at the outside of the axon membranes. The ECAP can then be measured in response to various stimulations and from this the performance of the implant can be assessed and patient parameters can be interpolated.

Indeed, there is a need to measure the response of nerves to electrical stimulation in many applications, and not just in the area of cochlear implants. The measurement of ECAPs has proven to provide a useful objective measurement in many such applications. By measuring the ECAP in response to a stimulation, the effectiveness of the stimulation can be assessed in relation to the neural response evoked by the stimulation.

A number of ECAP measurement methods and apparatus have been developed which attempt to measure the response of the nerves to electrical stimulus. In the area of cochlear implants where electrical stimulus is delivered to the nerve cells within the cochlea, such systems have essentially attempted to use the electrodes implanted within the cochlea to both deliver stimulation and to detect the responses of the nerves to such stimulation.

U.S. Pat. No. 5,758,651 describes one system and apparatus for recovering ECAP data from a cochlear implant. This system measures the neural response to the electrical stimulation by using the stimulus array to not only apply the stimulation but to also detect and receive the response. In this system the array used to stimulate and collect information is a standard intra-cochlear and/or extra cochlear electrode array. Following the delivery of a stimulation pulse via chosen stimulus electrodes, all electrodes of the array are open circuited for a period of time prior to and during measurement of the induced neural response. The purpose of open circuiting all electrodes during this period is to reduce the detected stimulus artefact measured with the ECAP nerve response.

Whilst prior art systems of this type have proven useful in capturing and investigating evoked neural responses in the cochlea, there are still a number of intrinsic limitations associated with such systems, which have affected the quality of the measurements of the neural response. In the main this has been due to the presence of stimulus artefacts in the measurement detected, resulting in a measurement being taken which is not necessarily a true indication of the actual ECAP response present.

The process of distinguishing the actual ECAP from stimulus artefacts has presented considerable difficulties, including problems such as the fact that the signals that are to be measured are extremely low level signals (down to the order of 10 uV). In cochlear implant applications in particular, an intra-cochlear electrode usually delivers a stimulus pulse with an amplitude typically in the range of 1V to 10V, which is many orders of magnitude greater than the ECAP response that is to be measured resulting from this stimulation.

Providing for a system that is firstly able to deliver a stimulus of sufficient amplitude and also to detect the elicited response of the nerves to that particular stimulation has therefore been problematic. Due to the nature of the neural response, the sensing system must be ready to record this response within a short delay (preferably less than 50 us) after completion of the stimulus. In order to properly resolve the very small neural signal a large amplifier gain is required (typically of about 60 dB to 70 dB), however the neural signal is often superimposed on a much larger artefact which makes it difficult to extract the neural signal of interest due to the finite dynamic range of the amplifier and the need for high gain to resolve the signal.

Prior to the present invention, the only way useful measurements have been able to be obtained from the associated artefacts has been through the use of extensive post processing techniques. These techniques have attempted to apply complicated mathematical algorithms to the associated measurements in an attempt to cancel out the presence of the artefacts in the measurements. Such a system does not provide immediate results which can be acted upon, as the measured results often require time consuming analysis before they can be used. With the need to use such results immediately to adjust patient T and C levels, existing methods are not satisfactory.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

SUMMARY OF THE INVENTION

According to a first aspect, the present invention provides a method of electrical artefact compensation in measurement of a neural response, the neural response evoked by a first stimulus, the method comprising the step of:

subsequent to the first stimulus, applying a compensatory stimulus in order to counteract a stimulus artefact caused by the first stimulus.

It has now been realised that stimulus artefacts in a nerve stimulus system arise due to a number of different mechanisms in the system and the surrounding tissue. The present invention, in addressing such artefacts at the time of attempting to measure evoked neural responses, allows for some reduction or compensation for the effects of stimulus artefacts, which can reduce or remove the need to resort to post-measurement processing.

In particular, it has been realised that stimulus artefacts arise due to charging of the tissue during stimulation. The first aspect of the present invention provides a method whereby compensation may be made for such artefacts. That is, application of the compensatory stimulus may prove effective in counteracting a residue charge distribution in the tissue caused by the first stimulus.

In preferred embodiments of the first aspect of the invention, the first stimulus comprises:

a first phase during which an electrical stimulus of first polarity is applied; and a second phase, subsequent to the first phase, during which an electrical stimulus of a second polarity opposite to the first polarity is applied.

Further, the first phase and second phase may be charge balanced.

In such embodiments, it has been realised that the tissue is charged in accordance with the first polarity during the first phase, and is charged in accordance with the second polarity during the second phase, and a residual charge may remain in the tissue following the second phase, for example due to spatial charge redistribution in the tissue during the stimulus. The residual charge contributes to the interface stimulus artefact. Accordingly, in such embodiments of the first aspect of the invention, the compensatory stimulus is preferably of the first polarity, and is preferably of controlled profile and duration, such as to compensate for the interface stimulus artefact. In such embodiments, the compensatory stimulus may be considered as a third phase stimulus.

Preferably, the compensatory stimulus is adaptive, in that characteristics of the compensatory stimulus are chosen in order to optimise the extent of cancellation of the artefact which exists following the first stimulus. Accordingly, the method of the first aspect of the invention preferably comprises the further step of:

determining characteristics of the compensatory stimulus from a measured effectiveness of a previously applied compensatory stimulus.

Such a step is preferably performed in an iterative manner, to provide an ongoing optimisation of the compensatory stimulus, based on the effectiveness of one or more previously applied compensatory stimuli. By performing an iterative determination of the characteristics of the compensatory stimulus, such embodiments of the present invention allow the compensatory stimulus to be adaptive.

In such embodiments, the measured effectiveness of the previously applied compensatory stimulus is preferably determined by:

obtaining at least one neural response measurement of an actual performance of the previously applied compensatory stimulus; and comparing the actual performance against a target performance, in order to determine an error between the actual performance and the target performance.

In more detail, the step of measuring the actual performance of the previously applied compensatory stimulus may comprise one or more of the following steps:

(i) applying the first stimulus and the previously applied compensatory stimulus, and subsequently obtaining a measurement comprising a first plurality of temporally spaced neural samples from a sensor, (ii) repeating step (i) in order to obtain a second plurality of measurements;

(iii) discarding an initial number of said second plurality of measurements to allow the sensor and other measurement components to settle;

(iv) averaging the remainder of the second plurality of measurements to obtain an averaged measurement; and (v) determining a stimulus artefect from the averaged measurement.

Step (i) may comprise obtaining 64 neural samples at 48 μs intervals (which is around 20 kHz), step (ii) may comprise obtaining 20 measurements, while step (iii) may comprise discarding the first 10 of said measurements, such that the averaged measurement is obtained from the remaining 10 measurements. The step of determining the stimulus artefact from the averaged measurement may comprise determining a deviation of the averaged measurement from a desired response.

The step of determining characteristics of the compensatory stimulus from the measured effectiveness of the previously applied compensatory stimulus is preferably performed by:

determining an incremental change to be made to characteristics of the previously applied compensatory stimulus in order to reduce the error between the actual performance and the target performance; and deriving the characteristics of the compensatory stimulus by altering the characteristics of the previously applied compensatory stimulus in accordance with the incremental change.

Preferably, the incremental change is determined so as to (a) maximise a rate of convergence of the actual performance to the target performance, and (b) minimise oscillation or overshoot of the actual performance relative to the target performance.

In many applications of the present invention, the compensatory stimulus will comprise a substantially rectangular pulse, the amplitude and duration of the pulse defining an amount of charge to be inserted by the pulse. Accordingly, in such embodiments, the incremental change preferably defines a change in the amount of charge which is required in order to improve the actual performance of the compensatory stimulus compared to the target performance. Further, for a given charge to be applied by the compensatory stimulus, the incremental change may further define whether a relatively narrow pulse of relatively large amplitude should be applied or whether a relatively broad pulse of relatively small amplitude should be applied in delivering the required amount of charge by the compensatory stimulus.

In preferred embodiments of the invention, the compensatory stimulus may be limited to having a variable amplitude only, and having a fixed duration. Such embodiments allow measurements subsequent to the compensatory stimulus to commence at a known time, regardless of an amount of charge to be delivered by the compensatory stimulus.

Preferably, the compensatory stimulus is completed prior to an expected time of commencement of an electrically evoked compound action potential.

In preferred embodiments of the first aspect of the invention, the neural response is the auditory nerve neural response, and the first stimulus is applied by an auditory prosthesis. The auditory prosthesis may comprise a cochlear implant with an intra-cochlear electrode array, including electrodes used as stimulus electrodes and/or as sense electrodes.

In embodiments where the auditory prosthesis is a cochlear implant comprising an electrode array, the first stimulus will typically be applied by one or more electrodes of the array, designated as stimulating electrodes. In embodiments of the first aspect of the invention, the compensatory stimulus will typically be applied by those same stimulating electrodes. However, it is to be appreciated that a compensatory stimulus may alternately or additionally be applied by other electrodes in the array. For example, application of additional, simultaneous compensatory stimuli may be appropriate in those electrodes in close physical proximity to the stimulating electrodes, due to the physical charge distribution caused by the first stimulus. The characteristics of such additional stimuli may be chosen responsive to an expected charge distribution in tissue adjacent to those different electrodes, caused by the first stimulus.

According to a second aspect, the present invention provides a method of electrical artefact compensation in measurement of a neural response, the neural response evoked by a first stimulus applied by at least one stimulating electrode, the method comprising the step of:

subsequent to the first stimulus, short circuiting at least each stimulating electrode to an electrode reference voltage.

It is preferable that the short circuiting of at least each stimulating electrode to an electrode reference voltage occurs for a short period of time, approximately 1 us, and preferably occurs immediately following the delivery of a compensatory stimulus such as is provided for by the first aspect of the present invention.

It is again noted that it has now been realised that stimulus artefacts in a nerve stimulus system arise due to a number of different mechanisms in the system and the surrounding tissue. The present invention, in addressing such artefacts at the time of attempting to measure evoked neural responses, allows for some reduction or compensation for the effects of stimulus artefacts, which can reduce or remove the need to resort to post-measurement processing.

Further, it has now been recognised that artefacts may arise in a stimulus system itself following a stimulus, and in particular may arise in electrodes of the system used for applying stimuli and/or electrodes of the system used for sensing a neural response. The second aspect of the present invention provides a method for compensating for such artefacts in the stimulating electrodes, by shorting the stimulating electrodes following application of the stimulus or a compensatory stimulus. Connection of the stimulating electrodes directly to the electrode array reference voltage quickly returns the stimulating electrodes to that voltage. Additionally, it has been realised that simply allowing passive tissue load settling, that is leaving all electrodes open circuited after a stimulus, increases the likelihood that the tissue voltage will stray from the electrode array reference voltage. In this event, subsequent connection of sensing electrodes for measurement of the neural response can occur at a time when a significant voltage difference exists between the actual tissue voltage and the electrode array reference voltage. At the time of connection of the sensing electrodes, such a voltage can give rise to significant charge injection into the sensing electrodes, potentially causing measurement of the actual neural response to be inaccurate or impossible and adding another source of artefact.

Preferably, the stimulus system is an auditory prosthesis for stimulus of the auditory nerve. It is anticipated that an auditory prosthesis in relation to which the method of the second aspect of the invention is used, will comprise an electrode array having multiple electrodes. For example, where the auditory prosthesis is a cochlear implant, the electrode array may comprise 22 to 30 intra-cochlear electrodes. In some embodiments of the invention, shorting of electrodes in the array other than the stimulating electrodes may be appropriate. For example, those electrodes in physical proximity to the stimulating electrodes may be influenced by charge build-up caused by the stimulating electrodes, and may therefore benefit from being short circuited for a brief settling period following the first stimulus, or following delivery of a compensatory stimulus. However it is possible that short circuiting a large number of electrodes in the electrode array following the first stimulus may lead to larger than acceptable current injection between the tissue and the electrodes. Hence, in many embodiments of the second aspect of the invention, only the stimulating electrodes are short circuited after application of a stimulus.

It will be appreciated that the method of the first aspect of the invention and the method of the second aspect of the invention may both be implemented to assist in reducing stimulus artefacts for a single measurement of neural response. In particular, the step of the second aspect of the invention may be performed after the step of the first aspect of the invention, and prior to commencement of measurement of the evoked neural response.

According to a third aspect, the present invention provides a neural stimulus system operable to apply a first stimulus in order to evoke a neural response, the neural stimulus system comprising means for electrical artefact compensation in measurement of the neural response, the means for electrical artefact compensation being operable to apply a compensatory stimulus in order to counteract a residue charge distribution caused by the first stimulus.

According to a fourth aspect, the present invention provides a neural stimulus system comprising at least one stimulating electrode operable to apply a first stimulus in order to evoke a neural response, the neural stimulus system being operable to compensate for electrical stimulus artefacts by short circuiting at least each stimulating electrode to an electrode reference voltage.

Preferably, measurement of the neural response is performed by detection of a signal present on designated sense electrodes. Preferably, the sense electrodes are different to the stimulus electrodes.

Preferably, the neural stimulus system is an auditory prosthesis, such as a cochlear implant. Preferably the response measured is the evoked compound action potential of the auditory nerve. The auditory prosthesis preferably comprises an array of intra-cochlear and extra-cochlear electrodes By compensating for stimulus artefacts, embodiments of the invention may assist in enabling high resolution neural response measurements to be acquired.

It has further been realised that application of a compensatory stimulus may prove to be of assistance generally when a first stimulus is applied to physiological tissue with a capacitive characteristic, where a response of the physiological tissue to the first stimulus is desired to be measured.

Accordingly, in a fifth aspect, the present invention provides a method of electrical artefact compensation in measurement of a physiological response, the physiological response evoked by a first stimulus, the method comprising the step of:

subsequent to the first stimulus, applying a compensatory stimulus in order to counteract a stimulus artefact caused by the first stimulus.

BRIEF DESCRIPTION OF THE DRAWINGS

Examples of the invention will now be described with reference to the accompanying drawings in which:

FIG. 3 is a circuit diagram illustrating an electrode array of an auditory prosthesis in accordance with the present invention;

FIG. 4a illustrates a stimulus artefact present following a bipolar stimulation, while

FIG. 6a illustrates the manner in which an MFD is obtained according to the present invention, while FIG. 6b illustrates the manner in which the polarity of a measured MFD may be determined;

DETAILED DESCRIPTION OF THE PREFERRED EMBODIMENTS

The following discussion will be made on the basis of the present invention being implemented in a cochlear implant, such as is discussed in U.S. Pat. No. 4,532,930, the contents of which are incorporated herein by reference. However, it is to be appreciated that the present invention may have application in other types of auditory prostheses and indeed may have application in measurement of neural responses, or in general, a physiological response to an electrical stimulation.

Figure 1:
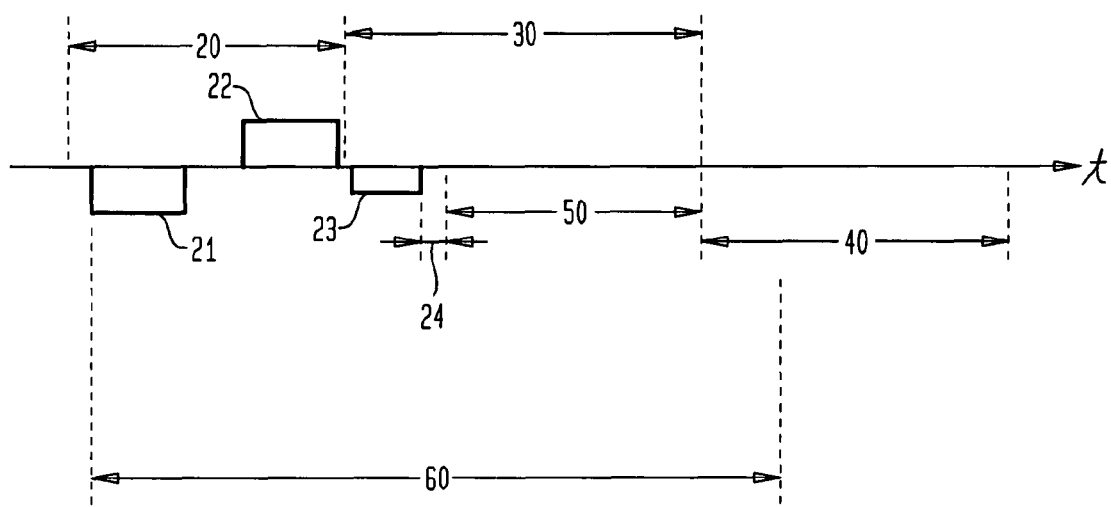
FIG. 1 illustrates a sequence of stimulus, artefact compensation and evoked neural response measurement in accordance with the present invention.

FIG. 1 illustrates the occurrence over time of a first stimulus 20, artefact compensation period 30 and evoked neural response measurement phase 40 in accordance with the present invention.

The first stimulus 20 includes a first phase 21 during which an electrical stimulus of negative polarity is applied by an intra-cochlear active stimulus electrode to the auditory nerve. Subsequently, a second phase 22 of positive polarity is applied by the active electrode. As will be appreciated, an intra-cochlear reference stimulus electrode may simultaneously apply complementary pulses. Alternatively, stimulation may occur with reference to all other electrodes of the electrode array, or with reference to an extra-cochlear electrode. It is to be noted that in this embodiment the first phase 21 and second phase 22 are of equal duration and amplitude and are therefore charge balanced. It is also envisaged that more than two phases of stimulation could be applied within the scope of the present invention. The first phase 21 and the second phase 22 could, for example, have a duration of the order of 15-50 µs, with an amplitude of up to around 10V. Further, first phase 21 and second phase 22 could be differently shaped, for example shaped as half sines, or as stepped half-sine approximations.

Subsequent to the stimulus 20, a third phase compensatory stimulus 23 is applied, in the present embodiment by the same active stimulating electrode, in order to counteract a residue charge distribution caused by the first stimulus 20. As noted above, it has been realised that the tissue in a cochlear implant system is charged by the negative pulse during the first phase 21, and is charged by the positive pulse during the second phase 22, and a relatively significant charge may remain following the second phase 22, for example due to charge redistribution during the stimulus. The remaining charge contributes to the tissue stimulus artefact. Accordingly, the compensatory stimulus 23 is of negative polarity.

The tissue artefact is mainly comprised of the effect of charge in the tissue which is left over from the stimulation and is being redistributed. The tissue artefact is most severe at the stimulus electrodes, but it will also couple to surrounding electrodes, dependent mainly on their proximity. For this reason the sense electrodes, to be used during measurement phase 40, are preferably selected to be different from the stimulus electrodes.

The amplitude and duration of compensatory stimulus 23 has been chosen in order to compensate for the interface stimulus artefact. As illustrated, compensatory stimulus 23 has a preselected amplitude and duration that is less than the amplitude and duration of the second phase 22 of the stimulus 20. In accordance with the invention, the compensatory stimulus 23 is adaptive, in that characteristics of the compensatory stimulus 23 are chosen depending on characteristics of the first stimulus 20. This is discussed further with reference to FIGS. 4 to 9 in the following.

Following compensatory stimulus 23, a load settling period 24 is applied, during which the stimulating electrodes are short circuited in accordance with the second aspect of the invention. Load settling period 24 is applied for approximately 1 us, however this period in FIG. 1 is not to scale with respect to the remainder of the Figure.

Load settling period 24 assists in compensating for artefacts which may arise in the stimulus electrodes of the implant by substantially restoring the tissue voltage and all internal stimulus and sensing circuit nodes back to the electrode array reference voltage. By shorting the stimulating electrodes following application of the stimulus 20 and compensatory pulse 23, the stimulating electrodes quickly return to the electrode array reference voltage. This method provides an alternative to allowing passive tissue load settling, in which all electrodes are left open circuited after a stimulus, which can increase the likelihood that the tissue will stray from the electrode array reference voltage. In such passive load settling, subsequent connection of sensing electrodes for measurement of the neural response can occur at a time when a significant voltage difference exists between the actual tissue voltage and the electrode array reference voltage. At the time of connection of the sensing electrodes, such a voltage can give rise to significant charge injection into the sensing electrodes, potentially causing measurement of the actual neural response to be inaccurate or impossible.

Programmable initial delay period 50 assists in dealing with cases whereby the tissue artefact is too large and exceeds the dynamic range of the amplifier. This delay period holds the amplifier in a reset state until start of measurement is desired. The delay period is usually set to the minimum value consistent with capturing the neural response signal.

The stimulus artefact caused by stimulus 20 is typically time-varying, and so the portion of signal present during measurement due to the artefact changes over time. Hence, the stimulus artefact introduces an artefact slew to measurements of the neural response. The third phase 23 or compensatory phase is preferably adjusted to minimise the artefact slew seen at the sensing electrodes, which may be either the same electrodes as those used for stimulation or which may be any of the other electrodes on the array. The parameters of this third or compensatory phase may be different for different sensing electrode positions, for example in response to space/time differences in the charge field. The system of the present invention is therefore capable of delivering a wide variety of stimulus waveforms which could be used dependant on the goals of the measurement and/or the manner in which the measurement is carried out.

The present embodiment of the invention manipulates the stimulus waveform applied prior to or during the measurement process in such a way as to minimise the artefacts associated with the measurement. As previously mentioned, in the present embodiment this is essentially done via the application of a smaller programmable third phase stimulus pulse immediately after the balanced biphasic stimulus, resulting in the system delivering an unbalanced triphasic stimulus.

The purpose of delivering this programmable third stimulus phase following the standard balanced biphasic stimulus pulse is to minimise or cancel the tissue artefact that would otherwise be present in the measurement, making it much easier to capture the neural signal at high amplifier gains, thereby allowing a higher resolution measurement of an ECAP response to be obtained. As the tissue artefact is mainly the effect of residual tissue potential (voltage) in the tissue which is left from the stimulation that is being redistributed, the third phase compensates for this. Preferably, characteristics of the third or compensatory phase are determined by taking into consideration the time-varying charge recovery nature of the tissue.

It is possible that the stimulus pulse could also be an unbalanced biphasic stimulus or a balanced triphasic stimulus, with the introduction of a compensatory phase performing the same function as is described above. Also, it is possible that the compensatory pulse may precede the stimulus and be non-rectangular or complex in shape and polarity. The invention resides in the provision of a compensatory stimulus to negate the effects of the tissue artefact and as such there are a number of different ways such a scheme may be implemented, all of which would fall within the scope of the present invention.

Figure 2:
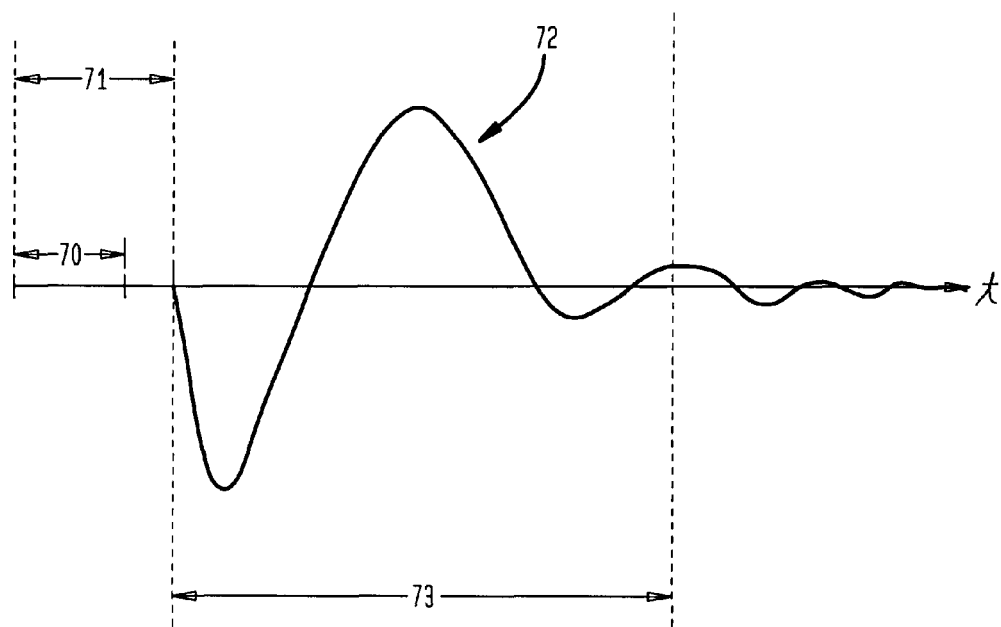
FIG. 2 illustrates a typical evoked neural response.

FIG. 2 illustrates a typical evoked neural response, which may arise in response to a stimulus 20 as depicted in FIG. 1. Period 70 in FIG. 2 illustrates a stimulation period, during which a stimulus is applied to an auditory nerve. The neural response 72 typically commences approximately 100 us after the onset of the stimulus phase 70, as indicated by period 71. The duration of the more significant features of the response is around 1000 us, as indicated by period 73, while the response measurement period or window is usually around 1.5 to 3 milliseconds.

Turning now to FIG. 3, a circuit diagram of an electrode array of a cochlear implant in accordance with the present invention is represented, by which the first stimulus 20, artefact compensation period 30 and evoked neural response measurement phase 40 may be applied. The electrode array is operable to apply the first stimulus 20 in order to evoke a neural response, and is operable to apply a compensatory stimulus 23 in order to counteract a residue tissue potential caused by the first stimulus 20. The electrode array is further operable to compensate for stimulus artefacts by short circuiting at least each stimulating electrode to an electrode array reference voltage, following application of a stimulus.

FIG. 3 illustrates four of the 24 electrode output switch networks and is merely an illustrative example of the system, to enable the operation of the circuit in its switching and sensing modes to be understood. Each of the four electrodes are indicated as A, B, C, D. As can be seen, each electrode can be connected to either the reference $V_{dd\_OS}$ line or the IO-line via switches S1 and S2 respectively, for each electrode. $V_{dd\_OS}$ represents the positive supply voltage rail for the output switches, $V_{ss}$ represents the negative supply rail and the IO-line represents the current source. The operation of these switches for the generation of charge balanced biphasic pulses is detailed in the applicants own U.S. Pat. No. 4,532,930.

For the present invention, each electrode has two additional switches (S3 and S4) to allow for connection to the sensing amplifier. In the quiescent state, all electrodes are usually short circuited to $V_{dd\_OS}$ to ensure long term charge recovery and no DC current. However, during the measurement period only the stimulating electrodes are shorted, for a very short time interval, in order to minimise current flow to the sensing electrodes which may introduce an unwanted stimulus artefact into the measurement.

The switch configuration of the present invention also includes another switch $S_{IPG}$ which is used in conjunction with an internal load resistor $R_{INT}$ to allow the IO-line to settle to a voltage close to $V_{dd\_OS}$ before the start of the stimulus phases. The purpose of allowing the IO-line to settle is to minimise the amplitude of the voltage spikes on the leading edge of the stimulus pulse due to the discharging of the IO-line capacitance into the load.

At the end of the third phase 23, there is a short load "settling period" 24, to restore the electrodes and the internal circuitry nodes back to as close to $V_{dd\_OS}$ as possible. In practice this load settling period can take a duration of ~1 us, and during this time the stimulation electrodes are shorted to $V_{dd_{OS}}$ by closing both the S1 switches. During this load settling period $S_{DAC}$ is also opened.

Following the load settling period the stimulation electrodes are opened leaving all electrodes in the open circuit state. The $V_{dd\_OS}$ switch is then opened thereby changing the circuit from the stimulation mode to the sensing mode. Following the above steps, measurement period 40 may proceed, after any appropriate initial delay 50. Importantly, measurement period 40 preferably commences prior to an onset of the neural response, so that obtained measurements record a leading edge of the neural response. The characteristic ECAP signal typically occurs approximately 100 us after the onset of the stimulus pulse 20 (as indicated by onset period 60 in FIG. 1) and usually has a duration of approximately 1000 us. It has been found that the signal's amplitude grows with the increasing number of nerve fibres captured as the amplitude of the stimulus increases above the threshold limit.

Measurement of the neural response is performed by detection of a signal present on designated sense electrodes of the implant. Preferably, the sense electrodes are different to the stimulus electrodes. By compensating for stimulus artefacts, embodiments of the invention may assist in enabling high resolution neural response measurements to be acquired.

Figure 4A:
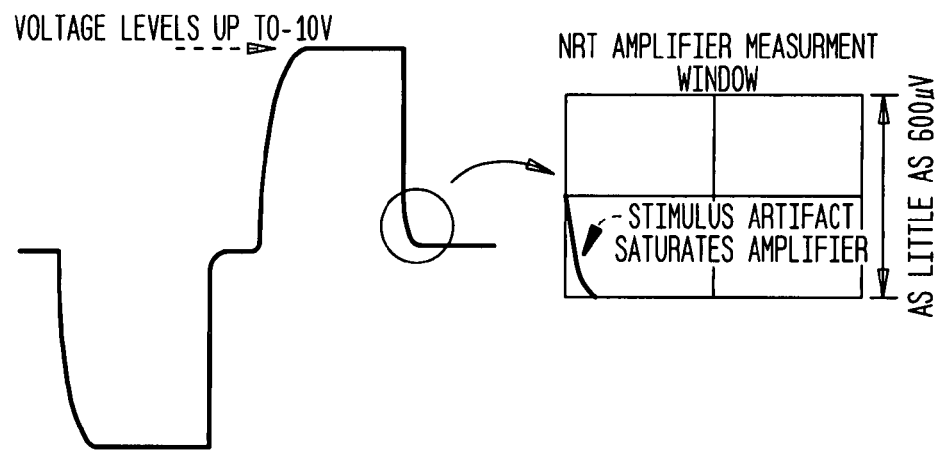

FIG. 4a illustrates a bipolar stimulation signal consisting of a first stimulation phase of negative polarity followed by a second stimulation phase of positive polarity, applied by an active electrode. Following the bipolar stimulation, a stimulus artefact is present. As can be seen, a significant stimulus artefact remains after the final charge has been delivered at the end of a standard two phase stimulus. This artefact has the effect of a gradual slewing or decay towards $V_{DD}$ which can be as large as of the order of millivolts at the relevant time and can take several hundred microseconds before becoming negligible. Given the extremely low level of neural response ECAP signals, down to the order of 10 microvolts, this significant remaining artefact can obscure the actual ECAP response, and can saturate the ECAP measurement system.

Figure 4B:
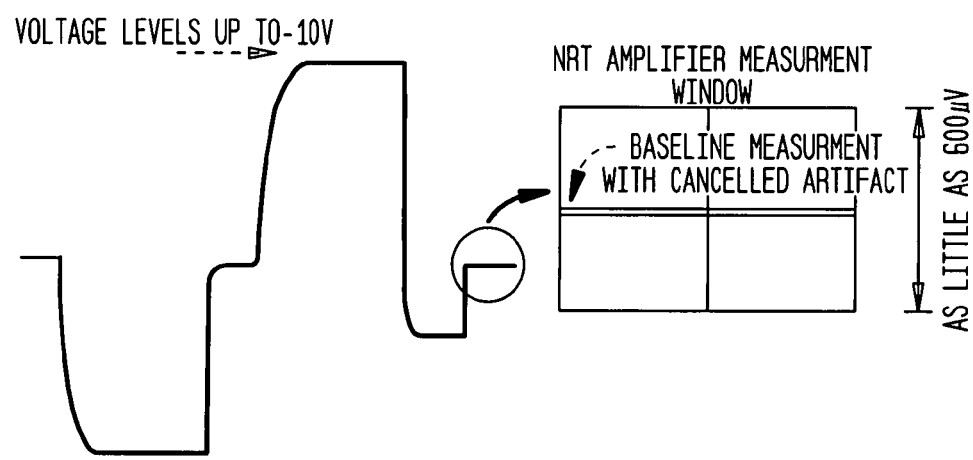
FIG. 4b illustrates the effect of a compensatory pulse.

FIG. 4b illustrates application of a compensatory stimulus, comprising a substantially rectangular pulse, of negative polarity. As opposed to FIG. 4a, at the time measurements commence, significant cancellation of the stimulus artefact has been achieved such that neural measurements are of the order of microvolts. As can be seen, application of the compensatory stimulus significantly hastens settling of the stimulus artefact, enabling a neural response measurement system or circuits to commence operation significantly more quickly following the bipolar stimulus, without saturation of the measurement system being caused by residual stimulus artefacts.

In applying a compensatory stimulus, it is important that the shape and characteristics of this stimulus are such that it does provide effective compensation for stimulus artefacts and that it does not worsen such artefacts. Consequently, the characteristics of the compensatory stimulus should be carefully determined. Given the detailed knowledge required of both the stimulus system and the patient physiology in order to perform such optimisation of the compensatory stimulus, manual adjustment of the parameters of the third phase would be a tedious and complicated process, which would not easily lend itself to clinical applications. Hence, in accordance with preferred embodiments of the invention, a method is proposed in order to address this problem, allowing the user to adjust parameters of the third phase without requiring extensive prior knowledge of the electrical workings of the electrode/tissue interface, thereby allowing convenient clinical use of such a system.

Figure 5:
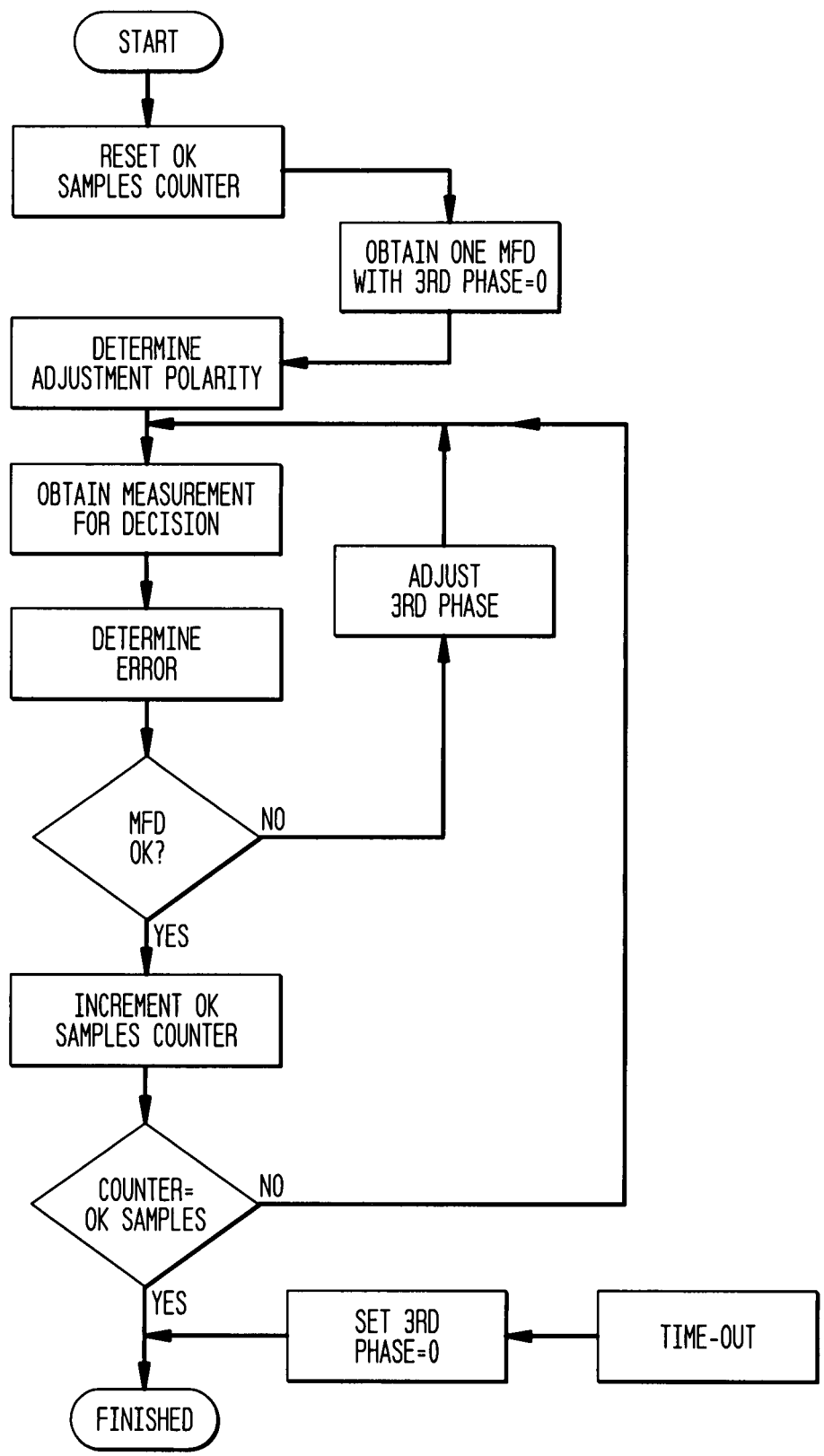
FIG. 5 is a flow chart illustrating the implementation algorithm of the resent invention.

Turning to FIG. 5, a flow chart is shown which reveals a manner of implementing an algorithm in accordance with the present invention, to optimise the parameters of the compensatory phase so as to appropriately cancel or counteract the effects of the stimulus artefact.

Firstly an OK Samples counter is set which determines the number of "correct" MFD's (Measurements for Decision) which must be obtained by the algorithm before the process can be considered to be complete. An MFD is considered to be correct when the error of the measurement is less than the tolerance set by the user, and this will be discussed in more detail below. In a preferred embodiment the counter would be set to require that four correct MFD's must be obtained before the adjustment of the compensatory means can be considered completed.

Subsequently, a first MFD is obtained, without the use of any compensatory phase. As the polarity of a measured MFD may swap depending on the manner in which sense electrodes are connected to the input of an amplifier, obtaining such an MFD allows the polarity of the measured MFD (denoted by variable P) and hence the manner in which the sense electrodes are connected to the input of the amplifier to be determined. FIG. 6b illustrates an output of a neural response detection amplifier for both positive and negative polarity situations. P takes a value of +1 or −1, and is subsequently used to influence whether an increase or decrease in charge applied by the compensatory phase should occur in response to a given error, as discussed further below.

The next step requires the MFD to be obtained, which in the present embodiment involves averaging 10 measurements, each comprising 64 collected telemetry samples in the manner as shown in FIG. 6a.

Following the delivery of the stimulus, including the compensatory stimulus, a series of telemetry measurements are taken of the evoked neural response. In a preferred embodiment 10 telemetry measurements are taken, each comprising 64 telemetry samples. It has been found that, following stimulation, the initial telemetry measurements tend to differ only slightly from the steady state telemetry measurements, however whilst there is only a very small settling period for the telemetry measurements it is wise to discard some initial telemetry measurements due to this phenomena. A preferred embodiment may be to discard the first 10 telemetry measurements.

It has also been found that to eliminate the effects of noise and telemetry measurement inaccuracies it is desirable to extract the MFD from an average of a number of telemetry measurements. In a preferred embodiment, 10 collected telemetry measurements are averaged from which the MFD is extracted.

The MFD that is obtained for example from a single measurement or from the average of a plurality of measurements is referred to as the "measurement for decision" (MFD) and it is this MFD that is used in the algorithm to decide upon the appropriate parameters of the compensatory phase. FIG. 6 illustrates how an MFD is obtained.

Once the MFD has been obtained an error is determined for the MFD, in order to determine whether the compensatory phase is appropriately adjusted. In the present embodiment, the error of a given MFD is determined by examining each point along the MFD to determine variations of the MFD from the target response. The variations at each point along the MFD are summed, and when the sum is equal to zero, that is when the MFD conforms to the target response or exhibits positive and negative excursions from the target response which sum to zero, the MFD is considered "correct". That is, the measured neural response substantially conforms to a target response, indicating that the stimulus artefact has been substantially cancelled. In accordance with such embodiments of the invention, the error of the MFD could be determined in accordance with the following algorithm:

Error(µs)=Σ[Sample $n$(µs)−First Sample(µs)−Target Offset(converted to µs)]

An alternate method in which the error of a given MFD may be determined is to simply calculate the difference between the first and last telemetry sample of the MFD. The difference between the first and last telemetry samples represents the amount by which the stimulus artefact has settled or decayed during the telemetry sample period, which is around three milliseconds in the present embodiment. As previously mentioned, in a preferred embodiment 64 telemetry measurements are used for this algorithm, to ensure that the majority of elements of the artefact and response have subsided from the measurement by the time the final sample is taken. Thus, where substantial subsidence of both the neural response and the stimulus artefact have occurred by the time the final sample is taken, the difference between the first sample and the final sample will be representative of the actual amplitude of the stimulus artefact present at the time the first sample is taken. This alternate method of determining the error of the MFD, could for example determine the error in us in accordance with the following formula:

Error(µs)=Last Sample(µs)−First Sample(µs)−Target Offset(converted to µs)

It should be appreciated that this is a very simplistic description of how the error is determined, for example, such a method assumes that there is a flat neural response, which is not usually the case. It is envisaged that other methods of determining the error in artefact cancellation could also be employed which do not make such simplifying assumptions of the present embodiment of the invention, such as by taking into account non-flat neural responses.

In both the preferred embodiment and in the latter alternate embodiment of determining the error of an MFD, the "Target Offset" variable indicates a deviation of the measurement from the desired target. The Target Offset is specified in µV and in a preferred embodiment this value should be set to 0 µV. In calculating the error the Target Offset variable is converted to µs.

Returning to FIG. 5, once the error of the MFD has been determined, an assessment is made as to whether the error of the MFD is acceptable. In the present embodiment, in assessing whether the MFD is acceptable the following criteria must be met:

|Error(µs)|≤Target Tolerance(µs)

The "Target Tolerance" variable essentially tightens or relaxes the criteria which determines whether or not an MFD is considered to be correctly adjusted or not. This variable is in units of microseconds and determines the tolerance in the pulse widths of the measured telemetry pulse in comparison to an ideal value. In a preferred embodiment this variable would alternate between a relaxed and a "normal setting, with the relaxed setting typically being 1.0 µs and the normal" setting being 0.2 µs. It is envisaged that the recommended default setting would be "normal".

If it is decided that the MFD is not acceptable and the error is outside the target tolerance, the compensatory phase is adjusted in order to bring the MFD to within acceptable limits. In essence, the amount of charge delivered by the compensatory phase is adjusted. This process is a two-step process with the first step involving the calculation of the new charge to be delivered by the compensatory phase, and the next step determining and calculating the corresponding values of phase width and phase current of the compensatory phase.

The new charge to be delivered by the compensatory phase is determined as follows:

New Charge(pC)=Old Charge(pC)+ΔCharge(pC)

Whereby

ΔCharge(pC)=Stepratio(nC/V)*Error(converted to V)*P

The "Stepratio" variable gives the rate at which the algorithm adjusts the compensatory phase charge in order to meet the required target measurement and describes the change in charge applied by the compensatory phase as a result of a given target error, the calculation of which is discussed above. In a preferred embodiment this variable is initially set at 1000 nC/V and any increase of this value will cause the algorithm to converge to the target faster but has the possibility of causing overshoot and oscillations, whilst any reduction in the value will cause slower but more stable convergence to the target measurement. P is the variable determined previously, relating to the polarity of connection of sense electrodes to the input of the amplifier.

Figure 7:
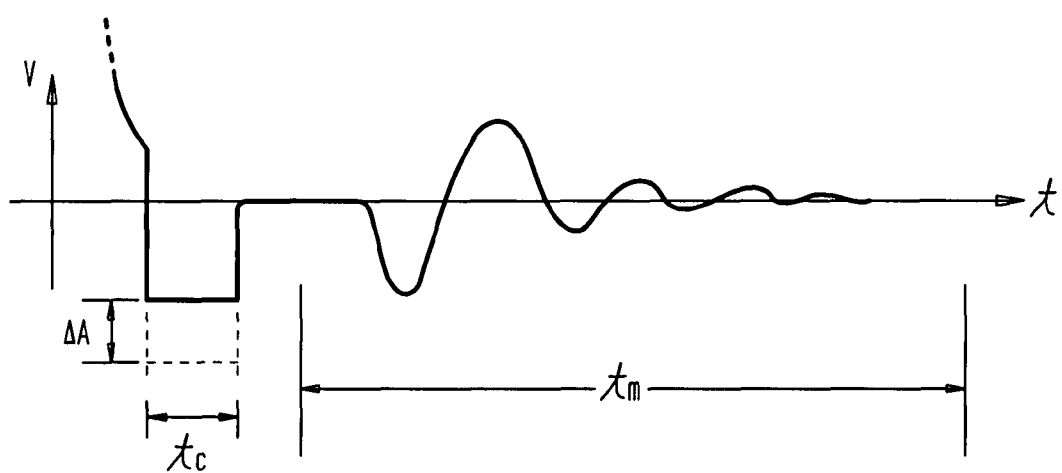
FIG. 7 illustrates the manner in which the compensatory pulse is varied in accordance with preferred embodiments of the invention.

In preferred embodiments of the invention, the compensatory stimulus as comprises a rectangular pulse of fixed duration $t_c$ and variable amplitude, as depicted in FIG. 7. To commence the adaptive optimisation of the compensatory pulse, an initial value of charge delivered by the compensatory pulse could be chosen arbitrarily, for example to be 20% of the charge delivered by one phase of the initial bi-phasic stimulus. As discussed above, the charge to be delivered by the compensatory stimulus is altered in accordance with the "stepratio" variable, which is implemented by altering the amplitude of the pulse, illustrated in an exaggerated manner in FIG. 7 by ΔA. By providing a compensatory stimulus of fixed duration, such embodiments of the invention allow the measurement period $t_m$ to commence at a known time, rather than requiring the measurement period to be delayed until completion of a variable duration compensatory pulse. FIG. 7 further illustrates the neural response to be measured, which is not to scale with respect to the compensatory stimulus.

Once the new charge to be delivered by the compensatory phase is determined, derivation of the 3rd phase current is a simple matter (bearing in mind that the compensatory pulse is of fixed duration), as follows:

3rd Phase Current(µA)=[3rd Phase Charge(pC)]/[3rd Phase Wdth(µs)].

The width of the third phase could be arbitrarily chosen, and for example could be of the order of 10 µs.

In alternate embodiments, should it be desired to use a compensatory stimulus of both varying width and amplitude, the corresponding values of phase width and phase current level to be delivered by the compensatory phase can be derived as follows:

Compensatory Charge(pC)=Compensatory Phase Width(µs)*Compensatory Phase Current(µA)

Figure 8:
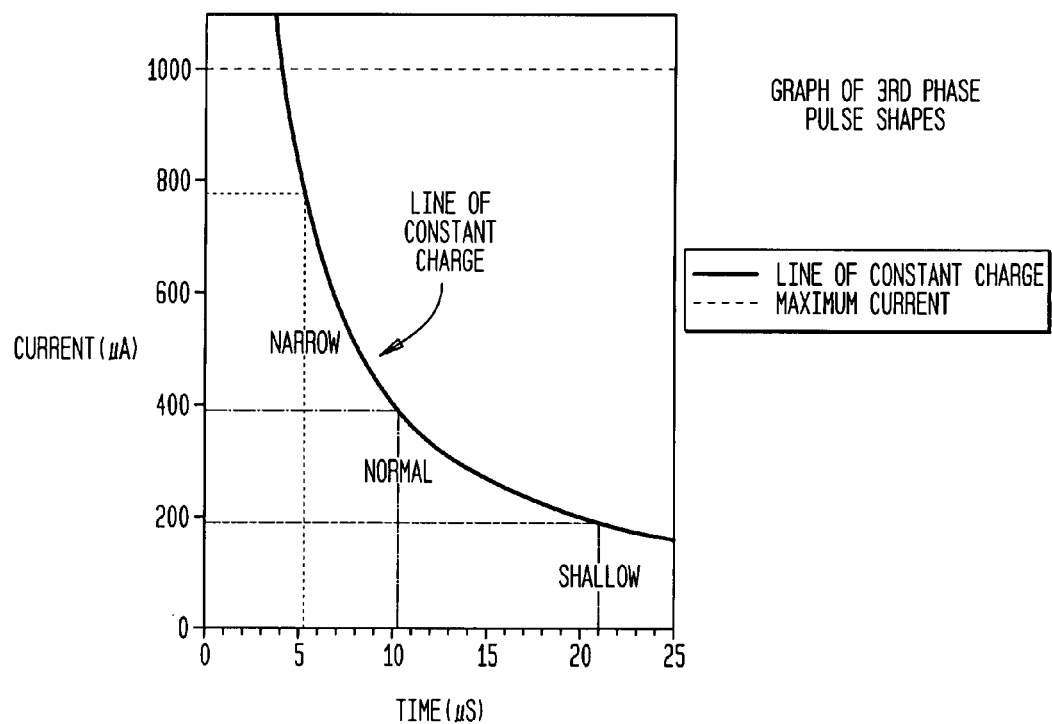
FIG. 8 illustrates possible compensatory phase shapes which may be applied in alternate embodiments of the present invention.

The relationship of the Compensatory Phase Width to the Compensatory Phase Current can be better understood by what is termed the Phase Shape variable. This variable is used to determine the "shape" of the compensatory phase. When selecting the shape of the compensatory phase it is possible to select almost any shape, however in the embodiment shown in FIGS. 8 and 9 a choice is made between a relatively narrow pulse, a relatively normal width pulse and a shallow pulse shape, to deliver a given charge. As can be seen in FIG. 8, a very narrow pulse has a much higher current/time compared to a low current/time characteristic of a shallow pulse, however the charge (l*t) delivered by all three shapes is the same. Therefore, whilst all these three shapes deliver the same charge, they have different ratios of l/t.

Figure 9:
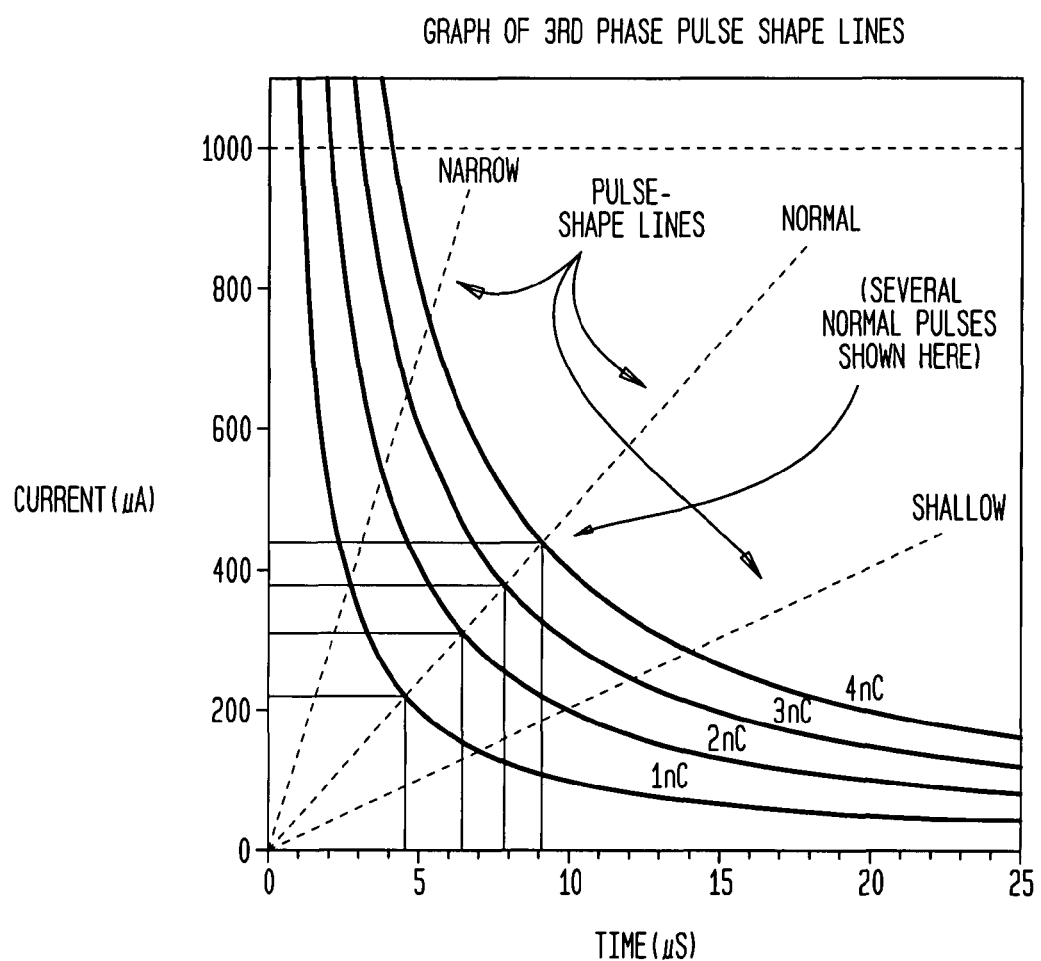
FIG. 9 shows equivalent pulse shape lines from FIG. 8 and their effect on pulse shapes of varying charge.

With this in mind, FIG. 9 shows equivalent pulse shape lines (l/t constant) and their effect on pulse shapes of varying charge. In essence for each of the three pulse shapes, narrow, normal and shallow, there is one value of l/t. In a preferred embodiment the values may be: Narrow −80 A/s, Normal −40 A/s and Shallow 20 A/s.

Therefore the following relationship can be established:

$$\frac{\text{Compensatory Phase Current (µA)}}{\text{Compensatory Phase Width (µs)}} = \text{Pulse Shape (A/s)}$$

From which the following relationship can be derived:

[Compensatory Phase Current(mA)]² =Compensatory Phase Charge(pC)*Pulse Shape(A/s)

Therefore from this the Compensatory Phase Width and Compensatory Phase Current can be determined and adjusted accordingly so that a new MFD can be obtained and assessed for error. However, it is to be appreciated that alternate embodiments of this type may prevent commencement of sampling at a common time for all values of pulse width, as commencement of sampling should not occur until after conclusion of the compensatory pulse.

Referring again to FIG. 5, if it is decided that the MFD is acceptable and the error is within the target tolerance, the OK Samples counter is incremented and the counter is then interrogated to determine whether the measurement process is complete and the desired number of correct MFD's has been measured.

If the number of correct MFD's is less than the desired number then the above measurement and error determination process is continued until this criteria has been satisfied.

When a desired number of correct MFD's have been obtained, a Time-out variable is applied to the algorithm which stops the algorithm from further adjustments after a specified time delay. In a preferred embodiment this time delay may be 5 seconds. Following this time the compensatory phase is set to zero and the process is completed. As can be seen, the described embodiments provide for adjustment of the characteristics of the compensatory phase without need for detailed user involvement. To provide differing levels of user input, the system may provide for user input of variables such as the number of telemetry measurements obtained per MFD, the Stepratio variable, and/or the pulse shape.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of electrical artifact compensation evoked by a first electrical stimulus, the method comprising:
    applying a first electrical stimulus to nerves using one or more first stimulating electrodes, the first electrical stimulus becoming subject to charge redistribution resulting in a stimulus artifact;
    configuring a compensatory electrical stimulus to substantially compensate for the stimulus artifact thereby reducing the stimulus artifact;
    applying the compensatory electrical stimulus to the nerves using one or more second stimulating electrodes, whereby the compensatory electrical stimulus is configured to improve measurement of a response of the stimulated nerves to the applied electrical stimuli;
    measuring a response of the stimulated nerves to the applied electrical stimuli using one or more sensing electrodes that are different than the one or more first and second stimulus electrodes; and
    altering a subsequent compensatory electrical stimulus based on the measured response.

2. The method of claim 1, further comprising measuring a response of the stimulated nerves to the applied electrical stimuli.

3. The method of claim 2, wherein measuring the response of the stimulated nerves includes measuring electrically evoked compound action potentials (ECAPs).

4. The method of claim 1, wherein the first electrical stimulus includes:
    a first phase having a first polarity;
    a second phase, subsequent to the first phase, having a second polarity opposite to the first polarity; and
    wherein the preselected amplitude and duration of the compensatory electrical stimulus is less than an amplitude and duration of the second phase of the first electrical stimulus.

5. The method of claim 4, wherein the compensatory stimulus is of the first polarity.

6. The method of claim 1, wherein the compensatory electrical stimulus is adaptive.

7. The method of claim 1, further comprising:
    waiting a predetermined period after the first electrical stimulus;
    after waiting a predetermined period, measuring an effectiveness of the compensatory electrical stimulus in compensating for said artifact; and
    altering a subsequent compensatory electrical stimulus in response to the measured effectiveness of the compensatory electrical stimulus.

8. The method of claim 7, wherein altering the subsequent compensatory electrical stimulus comprises:
    altering the amplitude and duration of the subsequent compensatory electrical stimulus.

9. The method of claim 7, further comprising:
    measuring an actual performance of the compensatory electrical stimulus in compensating for said artifact; and determining an error between the actual performance and a target performance.

10. The method of claim 9, wherein altering a subsequent compensatory electrical stimulus comprises:
    altering characteristics of the subsequent compensatory electrical stimulus by an incremental change, wherein the incremental change is adapted to reduce an error between an actual performance and the target performance.

11. The method of claim 10, wherein the incremental change is adapted to maximize a rate of convergence of the actual performance to the target performance.

12. The method of claim 11, wherein measuring the actual performance of the compensatory electrical stimulus comprises:
    applying the first electrical stimulus and the compensatory electrical stimulus; and
    measuring a first neural response resulting from the applied first and compensatory electrical stimuli, the first neural response including at least one first neural sample.

13. The method of claim 12, wherein measuring the first neural response includes:
    measuring approximately 64 first neural samples taken at approximately 48 microsecond intervals.

14. The method of claim 13, wherein measuring the actual performance of the compensatory electrical stimulus further comprises:
    repeating application of the first and compensatory electrical stimuli; and
    subsequent to each application of the first and compensatory electrical stimuli, measuring subsequent neural responses each including at least one second neural sample and resulting from respective applied first and compensatory electrical stimuli.

15. The method of claim 14, wherein measuring the subsequent neural responses comprises:
    measuring substantially 20 subsequent neural responses.

16. The method of claim 15, wherein measuring the actual performance of the compensatory electrical stimulus further comprises:
    discarding an initial number of the measured neural responses.

17. The method of claim 16, wherein discarding an initial number of the measured neural responses comprises:
    discarding approximately a first 10 of the measured neural responses.

18. The method of claim 17, wherein measuring the actual performance of the compensatory electrical stimulus further comprises:
    averaging un-discarded measured neural responses to obtain an averaged measurement.

19. The method of claim 18, wherein measuring the actual performance of the compensatory electrical stimulus further comprises:
    determining a stimulus artifact from the averaged measurement; and
    assessing an effectiveness of the compensatory electrical stimulus using the determined stimulus artifact.

20. The method of claim 19, wherein determining the stimulus artifact from the averaged measurement comprises:
    determining a deviation of the averaged measurement from a desired response.

21. A method of electrical artifact compensation evoked by a first electrical stimulus, the method comprising:
    applying a first electrical stimulus to nerves using one or more first stimulating electrodes, the first electrical stimulus becoming subject to charge redistribution resulting in a stimulus artifact;
    configuring a compensatory electrical stimulus to substantially compensate for the stimulus artifact thereby reducing the stimulus artifact;
    applying the compensatory electrical stimulus to the nerves using one or more second stimulating electrodes, whereby the compensatory electrical stimulus is configured to improve measurement of a response of the stimulated nerves to the applied electrical stimuli;
    short circuiting the one or more first and second stimulus electrodes;
    measuring, after the shorting, a response of the stimulated nerves to the applied electrical stimuli; and
    altering a subsequent compensatory electrical stimulus in response to a measured effectiveness of the compensatory electrical stimulus in compensating for said stimulus artifact.

22. The method of claim 21, wherein altering the subsequent compensatory electrical stimulus comprises:
    altering the amplitude and duration of the subsequent compensatory electrical stimulus.

23. The method of claim 21, wherein:
    the measuring includes:
        assessing an actual performance of the compensatory electrical stimulus in compensating for said stimulus artifact; and
    the method further comprises:
        determining an error between the actual performance and a target performance.

24. The method of claim 23, wherein altering a subsequent compensatory electrical stimulus comprises:
    altering characteristics of the subsequent compensatory electrical stimulus by an incremental change, wherein the incremental change is adapted to reduce an error between the actual performance and the target performance.

25. The method of claim 24, wherein the incremental change is adapted to maximize a rate of convergence of the actual performance to the target performance.

26. The method of claim 25, wherein measuring the actual performance of the compensatory electrical stimulus comprises:
    applying the first electrical stimulus and the compensatory electrical stimulus; and
    measuring a first neural response resulting from the applied first and compensatory electrical stimuli, the first neural response including at least one first neural sample.

27. The method of claim 1, wherein:
    the one or more first stimulating electrodes are the same as the one or more second stimulating electrodes.

28. The method of claim 21, wherein:
    only the one or more first and second stimulus electrodes are short circuited.

29. A method of objectively measuring one or more patient-specific parameters operating parameters of a cochlear implant, the method comprising:
    (a) applying a base electrical stimulus to nerves of the cochlea, the base electrical stimulus becoming subject to charge redistribution resulting in a stimulus artifact;
    (b) configuring a compensatory electrical stimulus to substantially compensate for the stimulus artifact;
    (c) applying the compensatory electrical stimulus to the nerves of the cochlea;
    (d) measuring a set of electrically evoked compound action potentials (ECAPs) of the stimulated nerves;
    (e) comparing variation of the set against a tolerance;

(f) adjusting, if the comparison is outside the tolerance, how the compensatory electrical stimulus is configured based on the comparison;
(g) looping back through steps (a)-(f) unless a loop-exit condition is satisfied; and
(h) determining, upon the condition having been satisfied, the one or more patient-specific parameters operating parameters based on the measured set of ECAPs.

* * * * *